US006428654B1

(12) United States Patent
Cronan, Jr. et al.

(10) Patent No.: US 6,428,654 B1
(45) Date of Patent: *Aug. 6, 2002

(54) FUNGICIDAL METHOD

(75) Inventors: John M. Cronan, Jr., Jacksonville, FL (US); Howard A. Cash, North Brunswick, NJ (US)

(73) Assignee: Hercules Incorporated, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/543,733

(22) Filed: Apr. 5, 2000

(51) Int. Cl.$^7$ .............................................. D21H 17/03
(52) U.S. Cl. .......................... 162/161; 161/72; 210/764
(58) Field of Search .............................. 162/157.2, 158, 162/160, 161, 164.1, 165, 166, 167, 173, 180, 183, 184, 185, 186, 189, 190, 5, 10, 11, 12, 70, 72, 199, 272, 163; 210/749, 764, 753

(56) References Cited

U.S. PATENT DOCUMENTS

| | | | |
|---|---|---|---|
| 2,901,394 A | 8/1959 | Rosher | 514/568 |
| 3,196,071 A | 7/1965 | Smith et al. | 162/161 |
| 3,896,236 A | 7/1975 | Brink, Jr. et al. | |
| 3,929,561 A | 12/1975 | Shema et al. | 162/161 |
| 3,976,495 A | 8/1976 | Buckman et al. | |
| 4,293,559 A | 10/1981 | Buckman et al. | 424/270 |
| 4,334,969 A | 6/1982 | Steglich et al. | 204/158 R |
| 4,914,128 A | 4/1990 | Schirmer et al. | 514/532 |
| 4,959,484 A | 9/1990 | Daum et al. | 539/334 |
| 5,003,101 A | 3/1991 | Brand et al. | 560/104 |
| 5,021,581 A | 6/1991 | Clough et al. | 546/309 |
| 5,055,417 A | 10/1991 | De Fraine et al. | 514/255 |
| 5,250,194 A | 10/1993 | Hollis et al. | 210/764 |
| 5,371,084 A | 12/1994 | De Fraine et al. | 514/241 |
| 5,432,197 A | 7/1995 | De Fraine et al. | 514/539 |
| 5,438,059 A | 8/1995 | Clough et al. | 514/256 |
| 5,607,597 A | 3/1997 | Wright et al. | 210/755 |
| 5,631,253 A | 5/1997 | De Fraine et al. | 514/243 |
| 5,736,056 A | 4/1998 | Wright et al. | 210/755 |
| 5,763,640 A | 6/1998 | De Fraine et al. | 560/35 |
| 5,942,528 A | * 8/1999 | Heil et al. | 514/361 |
| 6,090,831 A | * 7/2000 | Assmann et al. | 514/364 |
| 6,235,684 B1 | * 5/2001 | Knauf-Beiter et al. | 504/127 |

FOREIGN PATENT DOCUMENTS

| | | | |
|---|---|---|---|
| WO | 96/33611 | 10/1996 | A01N/25/28 |
| WO | 97/01277 | 1/1997 | A01N/43/828 |
| WO | 97/12520 | 4/1997 | A01N/43/54 |
| WO | 97/48671 | 12/1997 | C07C/67/307 |
| WO | 97/48692 | 12/1997 | C07D/311/76 |
| WO | 98/00021 | 1/1998 | A01N/57/20 |
| WO | 99 44424 A | 9/1999 | |

OTHER PUBLICATIONS

"Fungicides and Bactericides," downloaded on Aug. 8, 1999 from website: http://ecsoc2.hcc.ru/posters/dl001/fungicides.html.
Safety Data Sheet for Kresoxim–methyl, BASF, revised Jan. 6, 1999.
Cygnus Fact Sheet, NVA# 97–3–72–0001, BASF Corporation, 1997.
"Strobilurin Compositions," Research Disclosure entry 40585, Jan. 1998, pp. 90–94.
"Azoxystrobin Compositions," Research Disclosure, entry 39043, Oct. 1996, pp. 672–674.
"Synergistic Mixtures of Strobilurin and Pyrimidine Analogs," Research Disclosure, entry 38044, Dec. 1995, pp. 822–824.
"Strobilurin Analogues as Inhibitors of Mitochondrial Respiration in Fungi," J.M. Clough et al., in *Anti–infectives: Recent Advances in Chemistry and Structure–Activity Relationships*, P.H. Bentley et al., eds., pp. 176–179 (chapter 13), special publication of the Royal Society of Chemistry, No. 198, Cambridge, UK, 1997.
"Zeneca Invests in Its Amistar Fungicide," Chemical Week, Apr. 30, 1997, p. 34.
"U.K. Fungicide Approved," Chemical Week, Apr. 30, 1997, p. 8.
"BASF to Build Fungicides Unit in Spain," Chemical Week, Dec. 11, 1996, p. 25.
"Zeneca's Fungicide Sales Could Mushroom," Chemical Week, Dec. 4, 1996, p. 16.
"Zeneca Hitches Hopes on Mushrooms," Chemical Week, Nov. 25, 1996, p. 16.
"The Synthetic Strobilurin BAS 490 F: Profile of a Modern Fungicide", Modern Fungicides and Antifungal Compounds, Int. Symp., 11th, 1995 (published 1996).
"Efficacy of Strobilurine derivatives against grape powdery mildew in northern Italy," Chemical Abstracts entry 126:71520a.
"Azoxystrobin: Fate and effects in the terrestrial environment," Chemical Abstracts entry 126:71525f.
Printout from computer search using search term "Strobilurin".
Printout from computer search using search term "Azoxystrobin".
Sauter H. et al., "Strobilurins: Evolution of a New Class of Active Substances", Angewandte Chemie. International Edition, VCH Verlag, Weinheim, DE, vol 38, No. 10, 1999, pp. 1329–1346.

* cited by examiner

*Primary Examiner*—Peter Chin
*Assistant Examiner*—Eric Hug
(74) *Attorney, Agent, or Firm*—Joanne Rossi

(57) ABSTRACT

Use of strobilurins and oudemansins as biocides in aqueous systems is disclosed. Uses include wet-lap preservation, mold proofing, mildew proofing, and other uses where anti-fungal and/or anti-mildew activity is desired. Aqueous systems treatable with strobilurins and/or oudemansins include pulp and paper systems, oil and gas systems, cooling towers, and heat exchangers.

40 Claims, No Drawings

FUNGICIDAL METHOD

BACKGROUND OF THE INVENTION

1. Field of the Invention

This invention relates to the use of strobilurin antifungal agents, and to antifungals for use in industrial process waters, such as in the pulp and paper industries.

2. Discussion of Background

In many applications, such as industrial applications including the paper industry and in cooling towers, it is important to prevent or retard the growth of organisms, such as fungi, mildew, algae, protozoa and bacteria, in water or aqueous fluids. Biocides, e.g., fungicides, are used for this purpose. Fungicides, however, tend to be poorly water soluble, and so require special compositions for application in an intended use.

Fungicides are also important in industry in the area of wet-lap preservation. The term "wet-lap" refers to paper or other cellulosic product that is not completely dried after manufacture. Wet-lap is produced when paper destined for further processing may be maintained in a wet state until the further processing can begin. Where wet-lap is to be kept wet for an extended period, e.g., several days or more, the wet-lap can become subject to fungal or other biological attack. It is important, therefore, to preserve wet-lap by, e.g., application of an appropriate biocide, e.g., application of an antifungal composition.

Organic solvents used for fungicides in, e.g., in papermaking, can be noxious, volatile, flammable, and subject to regulation by governmental authorities. Fungicides such as Amical 48 (a formulation of diiodomethyl-paratolylsulfone) for example, are available in benzothiazole or in heavy aromatic naphtha.

Strobilurins form a class of biocides that is widely used in agriculture as crop protectants. The first strobilurins identified, strobilurins A and B, were isolated from the basidomycete *Strobilurus tenacellus* and *Crepidotus fulvotomentosus*. These antifungal compounds, which function by inhibiting mitochondrial respiration, were found to be quite efficacious as crop protectants in controlling numerous species of nuisance and pathogenic fungi, yet they exhibit low mammalian toxicity.

Because strobilurins have low solubility in water, they are commercially available as clay dispersions or microparticulate suspensions for application on crops, produce, and other agricultural products. For example, in U.S. Pat. No. 5,021,581, which is herein incorporated by reference in its entirety, there are disclosed strobilurin compositions comprising clay or talc in Examples 17–21. The document also discloses, in Example 16, a strobilurin composition comprising benzyl alcohol, calcium dodecylbenzene sulphonate, nonylphenolethoxylate, and alkyl benzenes.

Despite the wide range of biocidal activity exhibited by strobilurins, however, strobilurins have had limited use outside the agricultural arena. It is believed that the only use for strobilurins outside the agricultural arena has been limited use as a human and veterinary antifungal in a topical formulation. In particular, a strobilurin product has been used in a human and veterinary antifungal product under the name MUCIDERMIN SPOFA.

While strobilurin fungicides for use in agricultural settings, as noted above, can be formulated as clay or talc dispersions, in industrial settings, e.g., in process water systems, it is generally believed that fungicides for industrial use should be in the form of a solution rather than a dispersion. For this reason, among others, people outside the agricultural field would not look to agricultural fungicides.

Further, the presence of clay or talc is avoided in process water systems, e.g., in paper machines, because of the effects that such substances can have on machinery and product produced. In the case of paper machines, for example, the quantity and quality of clay and/or talc added, if any, is tightly controlled because these components can affect the quality of the paper product. Yet further, in cooling towers and heat exchangers, it is typically believed that clay or talc could present potential problems, e.g., clogging and abrasion of machine parts.

Fungicide compositions for use in a process water system, e.g., a paper machine or cooling tower, therefore, are generally formulated, as noted above, in organic solvents rather than as dispersions with, e.g., clay or talc.

Because of toxicity, volatility, and environmental concerns associated with fungicides formulated in volatile organic compounds, there is a need for safer fungicides and fungicide formulations for use in industry, such as in paper making, heat exchangers and cooling towers.

There is a need for biocidal compositions, e.g., antifungal compositions, for use in process water and/or process water systems, such as pulp and paper applications, and water cooling systems. There is also a need for biocidal methods, e.g., antifungal methods, for use in such systems.

There is a need for new antifungal methods for use in industrial systems, such as in pulp and paper systems, and in heat exchangers. Such methods include paper and wet-lap preservation, mold proofing, and cooling tower fluid preservation. Further, there is a need in systems such as these for biocidal compositions, e.g., antifungal compositions, that do not require use of volatile or flammable organic solvents.

SUMMARY OF THE INVENTION

It has now been surprisingly found that strobilurins, including novel formulations as well as commercially available clay dispersions and microparticulate dispersions, can be used in industrial systems for control of fungal growth.

The present invention provides a method for controlling growth of fungi or mildew comprising combining with an aqueous system a fungicide comprising a strobilurin, wherein the aqueous system comprises at least one of a papermaking machine, wet-lap, and a heat exchange system.

The present invention also provides a method for preserving wet-lap, the method comprising combining wet-lap and a fungicide comprising a strobilurin. The present invention also provides a method for preserving wet-lap comprising combining wet-lap and an effective anti-fungal amount of a strobilurin.

The present invention also provides a method for mold proofing or mildew proofing a cellulosic product, such as a paper product, the method comprising combining with the cellulosic product a composition comprising a strobilurin. The present invention also provides a method for mold proofing or mildew proofing a cellulosic product, such as a paper product, comprising combining with the cellulosic product an effective anti-fungal amount of a strobilurin.

The present invention also provides a paper product including an antifungal amount of a strobilurin.

Strobilurin according to the present invention can be any strobilurin or oudemansin having antifungal properties. The strobilurin preferably includes at least one of kresoxim methyl, azoxystrobin, Compound 5 (described below), strobilurin A, and strobilurin B.

Aqueous systems for methods and compositions of the present invention preferably include at least one of a papermaking machine and a heat exchange system. Included in the present invention are methods wherein the aqueous system comprises a papermaking machine comprising a stock tank, and the strobilurin is combined with fiber furnish in the stock tank. Also included are methods wherein the aqueous system comprises a papermaking machine comprising a pulp refiner, and the strobilurin is combined with fiber furnish in the pulp refiner. Also included are methods wherein the aqueous system comprises a papermaking machine comprising a stock chest, and the strobilurin is combined with fiber furnish in the stock chest. Also included are methods wherein the aqueous system comprises a papermaking machine comprising a flow box, and the strobilurin is combined with fiber furnish in the flow box. Also included are methods wherein the aqueous system comprises papermaking furnish, and the strobilurin is combined with the papermaking furnish. Also included are methods wherein the aqueous system comprises wet-lap, and the strobilurin is combined with the wet-lap.

Also included are methods wherein the aqueous system comprises a fluid in a heat exchange system, and the strobilurin is combined with the fluid. In a preferred embodiment, the heat exchange system comprises a cooling tower.

Where strobilurin is used in wet-lap, the strobilurin, or fungicide comprising strobilurin, is preferably present in the wet-lap in an effective antifungal amount. Preferably, the strobilurin is present in the wet-lap in a concentration of at least about 1 ppm, more preferably at least about 25 ppm, based on wet-lap at 50 wt % water content. Strobilurin is preferably present in the wet-lap at an upper concentration of less than about 5000 ppm, more preferably less than about 1000 ppm, more preferably less than about 500 ppm, based on wetlap at 50 wt % water content.

In a preferred embodiment, wet-lap is formed into a bulk article, and the strobilurin is applied to the bulk article at a level of at least about 20 mg/m$^2$, preferably at least about 30 mg/m$^2$, more preferably at least about 40 mg/m$^2$, based on surface area of the bulk article. Preferably, strobilurin is applied to the bulk article at a level preferably less than about 600 mg/m$^2$, more preferably less than about 300 mg/m$^2$ more preferably less than about 150 mg/m$^2$.

Wet-lap according to the present invention may be obtained from a fiber furnish comprising the fungicide.

Where strobilurin is applied to a cellulosic product, such as a paper product, preferably other than wet lap, it is preferred to apply an effective anti-fungal amount of the strobilurin. Such a cellulosic product preferably includes at least about 50 ppm strobilurin, more preferably at least about 100 ppm strobilurin, more preferably at least about 150 ppm strobilurin, based on dry weight of the paper product. For a paper product, preferably other than wet-lap, it is preferred to include about 1000 ppm or less strobilurin, more preferably about 500 ppm or less strobilurin, more preferably about 250 ppm or less strobilurin.

Where strobilurin is used in an aqueous composition such as a heat exchange system, strobilurin concentration is preferably greater than about 100 ppm, more preferably greater than about 200 ppm, more preferably greater than about 300 ppm, where the concentrations are based on weight of strobilurin per total weight of aqueous composition. Concentration of strobilurin in an aqueous composition such as a heat exchange system is generally about 5000 ppm or less, more preferably about 1000 ppm or less, more preferably about 500 ppm or less.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the invention may be embodied in practice.

All percent measurements in this application, unless otherwise stated, are measured by weight based upon 100% of a given sample weight. Thus, for example, 30% represents 30 weight parts out of every 100 weight parts of the sample.

Unless otherwise stated, a reference to a compound or component, includes the compound or component by itself, as well as in combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

Methods of the present invention include uses of compositions of the present invention to obtain biocidal, preferably antimicrobial, preferably antifungal and/or anti-mildew, activity. Compositions of the present invention can be used in pulp and paper systems; in heat exchange systems, such as cooling towers; and in oil and gas systems, preferably in pulp and paper systems.

The invention may be applied in any pulp and paper system, e.g., papermaking system, at any point in the system where fungicides can be employed, and in any manner that fungicides used in the paper industry can be employed. Compositions of the present invention, e.g., strobilurin compositions, may be employed directly, or in admixture with one or more other components. For example, in a papermaking application, a composition of the present invention can optionally contain one or more papermaking additives.

Also suitable is any combination of the foregoing locations, upstream of any of the foregoing locations, any point in between such locations, or any other suitable location, or combination of locations, concurrently or at different times.

Non-limiting examples of suitable aspects for use in a pulp and paper system include:

a) refined or unrefined furnish stock in stock tanks;
b) pulp refining conducted in a pulp refiner;
c) refined pulp stored in stock chests;
d) papermaking furnish drawn from stock chests; and
e) the flow box, the point at which the paper making furnish flows at a controlled rate onto the fourdrinier wire;
f) wet-lap preservation;
g) mold- and/or mildew-proofing;
h) size press;
i) coater section.

The present invention is further directed toward industrial use of antimicrobial compositions, preferably antifungal and/or anti-mildew compositions, comprising a strobilurin, preferably with at least one of a dispersive agent, coupling agent, and solubilizer. The invention is also directed toward methods of preparing the compositions, and methods of using them.

Unless otherwise stated, the terms "strobilurin" and "strobilurins" include any of the family of fungicidal substances known to those of ordinary skill in the art as the strobilurins, and includes strobilurins now known, as well as those not yet known. Further, as disclosed in Clough et al. (Clough, J. M., et al, "Strobilurin Analogues as Inhibitors of Mitochondrial Respiration in Fungi," in *Anti-infectives: Recent Advances in Chemistry and Structure-Activity Relationships*, P. H. Bentley et al., eds. Royal Society of Chemistry, pages 176–179, 1997), the disclosure of which is incorporated by reference in its entirety, the strobilurins are structurally related to the oudemansins, which also have biocidal activity. Thus, the term "strobilurins" should be understood herein as including biocides, e.g., fungicides, of the oudemansin family. The term also refers to mixtures of strobilurins, mixtures of oudemansins, and mixtures of at least one strobilurin and at least one oudemansin.

Any strobilurin or mixture of strobilurins may be used in a method or composition of the present invention. Strobilurins may be natural, semisynthetic, or synthetic. Some strobilurins are disclosed in "Natural Products in Crop Protection: fungicides," downloaded from website http://ecsoc2.hcc.ru/posters/d 1001/fungicides.html on Aug. 31, 1999, the disclosure of which is incorporated by reference herein in its entirety.

Natural strobilurins include those which are obtained from a fungal source, such as *Strobilurus tenacellus* and *Crepidotus fulvotomentosus*, and which are used without further chemical modification. Examples of natural strobilurins are strobilurin A and strobilurin B, which have the structure:

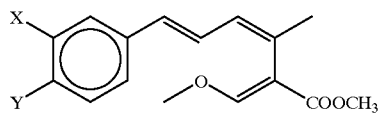

(1)

where X=H, Y=H for strobilurin A, and X=OCH$_3$, Y=Cl for strobilurin B. The natural strobilurins tend to be very photosensitive, which may shorten and/or lessen their effect if and when they are discharged into the environment.

Semisynthetic strobilurins include those which are chemically modified derivatives of one or more natural strobilurins.

Synthetic strobilurins include compounds in the strobilurin family which are not naturally occurring. These include kresoxim methyl (methyl (E)-2-methoxyimino-2-[2-(o-tolyloxymethyl) phenyl] acetate):

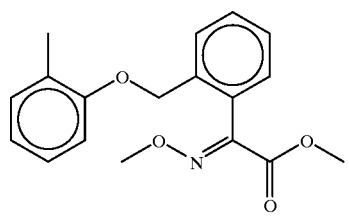

(2)

which is available from BASF; azoxystrobin:

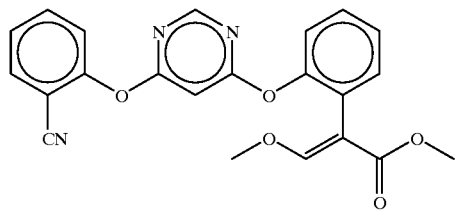

(3)

which is available from Zeneca; and SSF 126:

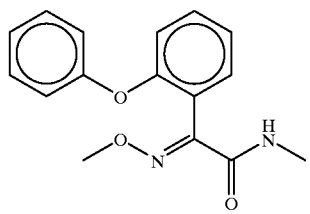

(4)

Yet another strobilurin is methyl (E)-2-[2-[6-(trifluoromethyl)pyrid-2-yloxymethyl]-phenyl]-3-methoxyacrylate, which has formula:

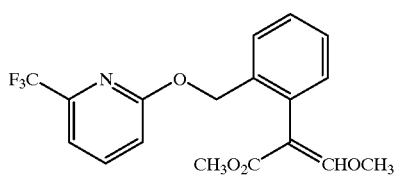

(5)

This strobilurin, which is believed to be produced by Zeneca, will be referred to herein as Compound 5.

Preferred strobilurins include kresoxim methyl, azoxystrobilurin, Compound 5, strobilurin A, strobilurin B, and mixtures thereof.

Kresoxim methyl is available from BASF in a technical grade at 94 wt % actives by weight. Kresoxim formulations are also available under the trade names CYGNUS (EPA File Symbol 7969-REU) and SOVRAN Fungicide (EPA File Symbol 7969-RLU), both of which are believed to contain active ingredient kresoxim methyl at 50.0 wt %. It is believed that both CYGNUS and SOVRAN comprise dispersions of kresoxim methyl in clay and surfactant. Azoxystrobin is commercially available from Zeneca under the trade names QUADRIS FLOWABLE Fungicide and HERITAGE.

While formulations of strobilurins such as those described above may be used, it should be noted that the present invention is not limited to the above strobilurin compositions. Strobilurin compositions for use in the present invention can comprise solubilizer, dispersive agent, and/or coupling agent. Further, any combination of solubilizer, dispersive agent, and coupling agent may be combined with a strobilurin composition, such as described above.

A solubilizer for use in the present invention can be any substance that increases the solubility of a strobilurin, or mixture of strobilurins, in water. Preferred solubilizers include benzyl acetate; N-methyl pyrrolidone; propylene carbonate; alcohols, such as benzyl alcohol, ethanol, methanol; and mixtures thereof.

As noted above, propylene carbonate can be utilized as a solubilizer for strobilurin. Compositions of propylene carbonate and strobilurin preferably have sufficient strobilurin to obtain biocidal, e.g., fungicidal, effect, preferably at least about 1 wt % of strobilurin with respect to propylene carbonate. Compositions of propylene carbonate and strobilurin preferably have up to about 40 wt % of strobilurin with respect to propylene carbonate, more preferably up to about 20 wt %, more preferably up to about 15 wt %, more preferably up to about 10 wt % strobilurin with respect to propylene carbonate. A particular strobilurin composition contains about 10 wt % strobilurin. For example, a particularly preferred composition of strobilurin and propylene carbonate contains about 9.4 wt % strobilurin with respect to propylene carbonate.

The choice of solubilizer can be made by one of ordinary skill in the art for each particular application, and different solubilizers can be preferred for different applications. For example, although an excellent solubilizer, propylene carbonate can have deleterious effects on paper machine press felts, and so would be less preferred in methods wherein a strobilurin composition contacts a paper machine press felt.

A dispersive agent may also be used in strobilurin compositions according to the present invention. Dispersive agents include any agent that promotes dispersion of strobilurin particles in a fluid medium. Some dispersive agents include, but are not limited to, surfactants, clay and talc.

Further, compositions of the present invention can also comprise a coupling agent. The coupling agent serves to act as an intermediary between strobilurin and solubilizing agent on the one hand, and an aqueous phase on the other hand. That is, the coupling agent couples with strobilurin and solubilizing agent, to increase the water dispersibility of the strobilurin, and to prevent strobilurin from crystallizing out. Any substance, or mixture of substances, that increases the water dispersibility of the strobilurin can be used as a coupling agent in methods and compositions of the present invention.

Coupling agents can comprise one or more polymers having hydrophilic and hydrophobic portions, such as hydrophilic polyalkylene polyols, hydrophilic cellulose derivatives. Some examples of polymeric coupling agents include polyethylene glycol (PEG), polypropylene glycol (PPG), hydroxyethyl cellulose (HBEC), hydroxypropyl cellulose (HPC), and mixtures thereof. Polyalkylene polyols and cellulose derivatives suitable for use in this invention are available from a variety of commercial sources.

When preparing a strobilurin composition having strobilurin in dissolved form, it is preferable to hasten dissolution of the strobilurin by agitation and/or warming the composition. When warming, it is preferable to warm the composition to a temperature that is below the temperatures of decomposition of each of the ingredients, and preferable to warm the composition to a temperature that is below the boiling temperature of the composition. For example, the composition may be warmed to a temperature preferably about 40–60° C., or higher. Warming and/or agitation may be accomplished in any manner.

As noted above, compositions for use in the present invention may comprise strobilurin dissolved in the composition, or in some other form, e.g., as a dispersion of strobilurin particles. Compositions that comprise strobilurin in dissolved form, e.g., compositions of strobilurin and propylene carbonate, are preferably stable to precipitation. By "stable to precipitation" is meant that no visible precipitation occurs when the composition is stored for extended periods (e.g., 24 hours, preferably 30 days or longer) at low temperatures (e.g., 5° C.).

The present invention includes both compositions, and uses of the compositions. As noted above, compositions of the present invention can be used in industrial systems, such as process water systems, including cooling systems, oil and gas systems, and pulp and paper systems. Industrial systems according to the present invention include systems in which a body of aqueous fluid is maintained in such a manner that fungi and/or mildew can grow. Such systems include, for example, pulp and paper systems (e.g., pulp furnish or wet-lap), heat exchange systems (e.g., water towers), and other industrial systems with sufficiently closed systems that organisms, e.g., fungi can grow. Growth of organisms such as fungi typically becomes detectable three to five days, or longer, after preparation of the aqueous fluid.

Preferred uses for compositions of the present invention are in pulp and paper systems. Some preferred uses in pulp and paper systems include uses in stock tanks; in pulp refiners; in stock chests; in paper making furnish; in flow boxes; in wet-lap preservation; and in mold- and/or mildew-proofing.

When used for wet-lap preservation, a composition of the present invention can be applied in any section of a paper machine, such as in the wet end or in the dry end. Preferred locations include a press section, e.g., a size press; or a coater section. Compositions can also be applied in any way, preferably with a roller or spray bar, preferably to formed paper.

The amount of strobilurin useful for wet-lap preservation can depend on a number of a factors, including the nature of the use and the conditions of use. Relevant factors include, e.g., the method of application, the nature of the fiber furnish, the types and amounts of additives used, the amount of water in the wet-lap, mill conditions, the type and species of organism(s) (e.g., fungi, mildew, *Aspergillus niger*, etc.) to be treated, storage conditions, light levels, and the expected length of time the wet-lap is to be preserved. The person of ordinary skill in the art is able to determine an appropriate level of strobilurin for wet-lap preservation for a particular application, and any biocidal amount of strobilurin may be used.

When used for wet-lap preservation, strobilurins can be applied to wet-lap in any manner by one of ordinarily skill in the art. Generally, however, wet-lap is preferably preserved by either of two preferred methods. According to one method, referred to herein as internal wet-lap preservation, strobilurin is applied to the wet-lap before the wet-lap is formed into a bulk article, such as a roll or bale. In this method, strobilurin is preferably substantially uniformly distributed throughout the bulk wet-lap article. When this method is used, an effective antifungal and/or anti-mildew amount of strobilurin for wet-lap preservation is preferably applied, preferably greater than about 1 ppm, more preferably greater than about 25 ppm, where ppm for wet-lap refers to weight of strobilurin per weight of wet-lap (measured at 50 wt % water) multiplied by one million. There is no preferred upper limit of strobilurin content, but for reasons of cost, strobilurin concentration is preferably less than about 5000 ppm, more preferably less than about 1000 ppm, more preferably less than about 500 ppm.

In another preferred method of wet-lap preservation, referred to herein as external wet-lap preservation, wet-lap is first formed into a bulk article, e.g., a roll or bale. Then, a strobilurin composition is applied to the surface of the roll or bale. This method may be more economical as less strobilurin is used per roll or bale of wet-lap. It is believed that this method still satisfactorily preserves wet-lap as strobilurin is concentrated on the surface of the bale, where fungi may settle, e.g., during storage. When this method is used, strobilurin may be applied in any effective antifungal and/or anti-mildew amount. Generally, however, the amount of strobilurin will be at least about 20 mg/m$^2$, preferably at least about 30 mg/m$^2$, more preferably at least about 40 mg/m$^2$, where the amounts are expressed as mg strobilurin per m$^2$ of wet-lap bulk article surface area. There is no preferred upper limit of strobilurin content, but for reasons of cost, strobilurin concentration is preferably less than about 600 mg/m$^2$, more preferably less than about 300 mg/m$^2$, more preferably less than about 150 mg/m$^2$.

Of course, the internal and external methods of wet-lap preservation can be combined, with antifungal and/or anti-mildew agent applied both internally and externally. When both internal and external wet-lap preservation methods are used, preferably at least one of the internal and external methods employs strobilurin according to the present invention. Preferably, strobilurin is used in both internal and external methods when the two methods are combined. One of ordinary skill in the art will appreciate that when both internal and external wet-lap preservation methods are used, lower levels of internal and/or external addition than disclosed above can be employed.

When applied to paper products other than wet-lap, strobilurin concentration is measured as parts per million (ppm) on a dry weight basis. When applied to paper product other than wet-lap any effective anti-fungal and/or anti-mildew amount of strobilurin may be applied. It is preferred to apply at least about 50 ppm strobilurin, more preferably at least about 100 ppm strobilurin, more preferably at least about 150 ppm strobilurin. For paper product other than wet-lap, it is preferred to apply about 1000 ppm or less strobilurin, more preferably about 500 ppm or less strobilurin, more preferably about 250 ppm or less strobilurin.

When combined with water, e.g., in a cooling tower, or prior to application to paper, it is preferred to use a sufficiently high concentration of strobilurin to obtain antifungal and/or anti-mildew activity. The concentration of strobilurin required to obtain a sufficient level of antifungal and/or anti-mildew activity can vary depending on the system treated and the strobilurin used. The person of ordinary skill in the art is able to determine an appropriate concentration of strobilurin in water, aqueous fluid, or process water for a particular application. Generally, however, an effective antifungal and/or anti-mildew concentration of strobilurin in water, aqueous fluid, or process water, is greater than about 100 ppm, more preferably greater than about 200 ppm, more preferably greater than about 300 ppm, where the concentrations are based on weight of strobilurin per total weight of composition. Use of too much strobilurin results in wasted material. Thus, concentration of strobilurin in water, aqueous fluid, or process water, is generally about 5000 ppm or less, more preferably about 1000 ppm or less, more preferably about 500 ppm or less.

EXAMPLES

The present invention will be further illustrated by way of the following Examples. These examples are non-limiting and do not restrict the scope of the invention.

Unless stated otherwise, all percentages, parts, etc. presented in the examples are by weight.

Example 1

A composition of the components listed in Table 1 is prepared by adding 150 mg benzyl acetate (Janssen Chimica, Geel, Belgium) to kresoxim methyl (100 mg, technical grade (94 wt % actives), from BASF Corporation, Ludwigshafen, Germany). This mixture is placed into a test tube and run under hot tap water to assist dissolution of kresoxim methyl. To this solution, 750 mg of PEG 400 (Acros Chemical, Fair Lawn, N.J.) is added to complete the blend.

TABLE 1

| Component | percent by weight |
|---|---|
| kresoxim methyl (techhical grade) | 10% |
| benzyl acetate | 15% |
| PEG-400 | 75% |

Example 2

A 100 mg sample of kresoxim methyl (technical grade, BASF Corporation, Ludwigshafen, Germany) is added to 900 mg propylene carbonate (Sigma Chemical, Saint Louis, Mo.). This mixture is placed into a test tube and run under hot tap water to assist dissolution of kresoxim methyl.

Example 3

Preparation of the Spore Inoculum—Two sterile petri dishes containing potato dextrose agar are inoculated with *Aspergillus niger* (ATCC 6275). The plates are incubated for at least 48 hours at 35+1 ° C. At the end of the incubation period, the plates are checked for mycelia and fruiting bodies of the fungus. To prepare the spore-mycelial suspension, the agar surface is scraped with a sterile cotton tip swab. The spores are suspended from the cotton swab in a sterile test tube containing a solution of 0.85% saline and 0.01% Tween 80 (v/v). The spore-mycelial suspension is shaken or vortexed to break up spore and mycelial clumps. Prior to the addition of the spore-mycelial suspension to the test tube containing saline and Tween, a spectrophotometer is set to 650 nm and the absorbance reading is balanced to zero. The optical density (absorbance) of the spore-mycelial suspension is measured in the spectrophotometer. If necessary, the optical density is adjusted to 0.29 absorbance units by addition of diluent or spores. At an optical density of 0.29 absorbance units (at 650 nm), the concentration of spores is 1×10$^9$ spores/ml. The spore-mycelial suspension is diluted 1/1000 to yield inoculum used for the microtiter assay, having a concentration of 1×10$^6$ spores/ml.

Microtiter Assay—Six MULTISCREEN filtration plates (96-well MULTISCREEN-GV, clear plates with 0.22 μm membrane; Millipore Corp., Molsheim, France) are used for a three dose response protocol. This protocol and the six MULTISCREEN plates allows for duplication of the experimental results. The three actives employed are BAS49002F (kresoxim methyl at 50 wt %; BASF Corporation, Ludwigshafen, Germany), AF1912 (diiodomethyl-paratolylsulfone; Angus Chemical Company, Buffalo Grove, Ill.), and MBTC (methylenebisthiocyanate; Aldrich Chemical Company, Milwaukee, Wis.). These actives are individually diluted with water to a concentration of 40 ppm actives. Using separate dilution blocks for each active, the actives are serially diluted to reach experimental dose ranges from 10 to 0.156 ppm. Along with the treatments (actives), Sabouraud Dextrose broth (DIFCO Laboratories, Detroit Mich.) and inoculum are added to each well. The microtiter plates are incubated at 37° C. for 24 hours, and after this period a 0.1% solution of XTT (2,3-bis[2-methoxy-4-nitro-5-sulfophenyl]-2H-tetrazolium-5-carboxanilide; Sigma Chemical, Saint Louis, Mo.) and 0.01% of PMS (phenazine methosulfate; Sigma Chemical, Saint Louis, Mo.) are added to each well. The plates are incubated for approximately 3 more hours. Filtration via the MULTISCREEN plates removes the mycelial growth and nonvegetated spores of *Aspergillus niger*. Each microtiter well is read at 465 nm for the reduction of XTT by metabolically active cells (i.e., a color change from the untreated controls would indicate respiring fungal cells). Growth inhibition results are presented in Table 2, which represents the processed absorbance data that has been converted as a percent inhibition of fungal growth by the three actives tested (BAS49002F, AF1912, and MBTC). The dashed lines in Table 2 indicate negative inhibition values, which indicate that cells were viable, but in futile cell cycles.

TABLE 2

| Antifungal | Sample | Conc. (ppm) | | | | | | |
| --- | --- | --- | --- | --- | --- | --- | --- | --- |
| | | 0.156 | 0.31 | 0.625 | 1.25 | 2.5 | 5.0 | 10.0 |
| BAS49002F (composition of kresoxim methyl at 50 wt % in clay dispersion; BASF) | Plate 1 | 5 | 21 | 48 | 65 | 70 | 73 | 69 |
| | Plate 2 | 12 | 34 | 53 | 65 | 69 | 71 | 58 |
| AF1912 | Plate 1 | 20 | 24 | 38 | 89 | 89 | 89 | 89 |
| Amical Flowable 1912 | Plate 2 | 24 | 36 | 37 | 87 | 88 | 88 | 88 |
| MBTC | Plate 1 | — | — | — | — | 86 | 88 | 88 |
| methylene bisthiocyanate | Plate 2 | — | — | — | — | 84 | 89 | 89 |

The strobilurin composition designated BAS49002F is very active as demonstrated by the results of the screening assay (Table 2). It is believed that the apparently better performance of Amical is due, in part, to the assay employed to evaluate the performances of the actives.

Example 4

Qualitative experiments are conducted in which two kresoxim methyl compositions available from BASF (BAS49002F and BAS49011F; BASF Corporation, Ludwigshafen, Germany) are added at 50 and 100 ppm concentration to wet-lap sheets that had been inoculated with a spore-mycelial suspension of *Aspergillus niger*. The 0.5 wt % consistency pulp is prepared from 70% bleached hardwood and 30% bleached softwood fibers. To individual portions of this stock, chemical treatments of BAS49002F and BAS49011F are added at concentrations of 50 and 100 ppm strobilurin, based on weight of dry weight basis of fiber. Handsheets (water content about 50 wt %) are formed using a Britt jar. Three handsheets are prepared for each concentration and for each active, as well as the untreated control. The handsheets are handled aseptically to minimize bacterial contamination. A 2"×2" square is aseptically cut and transferred to potato dextrose agar plates (DIFCO Laboratories, Detroit, Mich.). One milliliter of spore inoculum (see Example 3—Preparation of Spore Inoculum) is distributed over the top of each wet-lap sheet via pipet. Plates are sealed with PARAFILM (American National Can, Menasha, Wis.), and incubated at 35° C. for seven days. Observations are recorded daily for growth and sporulation. Both of the compositions (BAS49002F and BAS49011F) at 50 and 100 ppm prevent growth of *Aspergillus niger* on potato dextrose agar plates up to day 4 under these conditions, but fungal growth is observed after this period.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A method for controlling growth of fungi or mildew comprising combining with an aqueous system a fungicide comprising a strobilurin, wherein the aqueous system comprises at least one of a papermaking stock tank, pulp refiner, stock chest, flow box, furnish, and wet-lap.

2. The method of claim 1 wherein the aqueous system comprises a papermaking stock tank, and the strobilurin is combined with fiber furnish in the stock tank.

3. The method of claim 1 wherein the aqueous system comprises a papermaking pulp refiner, and the strobilurin is combined with fiber furnish in the pulp refiner.

4. The method of claim 1 wherein the aqueous system comprises a papermaking stock chest, and the strobilurin is combined with fiber furnish in the stock chest.

5. The method of claim 1 wherein the aqueous system comprises a papermaking flow box, and the strobilurin is combined with fiber furnish in the flow box.

6. The method of claim 1 wherein the aqueous system comprises papermaking furnish, and the strobilurin is combined with the papermaking furnish.

7. The method of claim 1 wherein the aqueous system comprises wet-lap, and the strobilurin is combined with the wet-lap.

8. The method of claim 7 wherein the strobilurin is present in the wet-lap in a concentration of at least about 1 ppm, based on wet-lap at 50 wt % water content.

9. The method of claim 8 wherein the strobilurin is present in the wet-lap in a concentration of at least about 25 ppm, based on wet-lap at 50 wt % water content.

10. The method of claim 7 wherein the strobilurin is present in the wet-lap in a concentration of about 5000 ppm or less, based on wet-lap at 50 wt % water content.

11. The method of claim 7 wherein the wet-lap is formed into a bulk article, and the strobilurin is applied to the bulk article at a level of at least about 20 mg/m$^2$, based on surface area of the bulk article.

12. The method of claim 11 wherein the strobilurin is applied to the bulk article at a level of at least about 30 mg/m$^2$, based on surface area of the bulk article.

13. The method of claim 12 wherein the strobilurin is applied to the bulk article at a level of about 600 mg/m$^2$ or less, based on surface area of the bulk article.

14. The method of claim 1 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

15. A method for controlling growth of fungi or mildew comprising combining with an aqueous system an effective anti-fungal amount of strobilurin, wherein the aqueous system comprises at least one of a papermaking stock tank, pulp refiner, stock chest, flow box, furnish, and wet-lap.

16. The method of claim 15 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

17. The method of claim 15 wherein the aqueous system comprises a papermaking stock tank, and the strobilurin is combined with fiber furnish in the stock tank.

18. The method of claim 15 wherein the aqueous system comprises a papermaking pulp refiner, and the strobilurin is combined with fiber furnish in the pulp refiner.

19. The method of claim 15 wherein the aqueous system comprises a papermaking stock chest, and the strobilurin is combined with fiber furnish in the stock chest.

20. The method of claim 15 wherein the aqueous system comprises a papermaking flow box, and the strobilurin is combined with fiber furnish in the flow box.

21. The method of claim 15 wherein the aqueous system comprises papermaking furnish, and the strobilurin is combined with the papermaking furnish.

22. The method of claim 15 wherein the aqueous system comprises wet-lap, and the strobilurin is combined with the wet-lap.

23. A method for preserving wet-lap, the method comprising combining wet-lap and a fungicide comprising a strobilurin.

24. The method of claim 23, wherein the fungicide is combined with the wet-lap at a concentration between about 1 ppm and 5000 ppm strobilurin, based on weight of wet-lap at 50% water content.

25. The method of claim 23 wherein the wet-lap is formed into a bulk article, and the strobilurin is applied to the bulk article in an amount between about 20 mg/m$^2$ and 600 mg/m$^2$, based on surface area of the bulk article.

26. The method of claim 23 wherein the wet-lap is obtained from a fiber furnish comprising the fungicide.

27. The method of claim 23 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

28. A method for mold proofing or mildew proofing an article comprising a paper product, the method comprising combining with an article comprising a paper product a composition comprising a strobilurin.

29. The method of claim 28, wherein the paper product comprises about 1000 ppm or less of strobilurin on a dry weight basis.

30. The method of claim 28 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

31. A paper product including an antifungal amount of a strobilurin.

32. The paper product of claim 31 including at least about 50 ppm of the strobilurin on a dry weight basis.

33. The paper product of claim 32 including about 1000 ppm or less of the strobilurin on a dry weight basis.

34. The paper product of claim 31 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

35. A method for controlling growth of fungi or mildew comprising combining with an aqueous system an effective antifungal amount of fungicide comprising a strobilurin, wherein the aqueous system comprises at least one of a papermaking machine and a heat exchange system.

36. The method of claim 35 wherein the aqueous system comprises a fluid in a heat exchange system, and the strobilurin is combined with the fluid.

37. The method of claim 36 wherein the heat exchange system comprises a cooling tower.

38. The method of claim 36 wherein the strobilurin has a concentration of at least about 100 ppm based on weight of the fluid.

39. The method of claim 35 wherein the aqueous system comprises a fluid in at least one of a papermaking stock tank, pulp refiner, stock chest, flow box, and furnish, and the strobilurin is combined with the fluid.

40. The method of claim 35 wherein the strobilurin includes at least one of kresoxim methyl, azoxystrobin, methyl (E)-2-[2-[6-(trifluoromethyl)pyrid-2-yloxymethyl]-phenyl]-3-methoxyacrylate, strobilurin A, and strobilurin B.

* * * * *